United States Patent [19]

Navia et al.

[11] Patent Number: 5,530,106
[45] Date of Patent: Jun. 25, 1996

[54] RECOVERY OF SUCRALOSE INTERMEDIATES

[75] Inventors: Juan L. Navia, Athens; Robert E. Walkup, Watkinsville; David S. Neiditch, Athens, all of Ga.

[73] Assignee: McNeil-PPC, Inc., Skillman, N.J.

[21] Appl. No.: 368,466

[22] Filed: Jan. 4, 1995

Related U.S. Application Data

[63] Continuation of Ser. No. 198,744, Feb. 18, 1994, abandoned, which is a continuation-in-part of Ser. No. 30,518, Mar. 12, 1993, Pat. No. 5,298,611.

[51] Int. Cl.⁶ .......................... C07H 13/04; C07H 13/06; C07H 13/00
[52] U.S. Cl. .......................... 536/4.1; 536/115; 536/119; 536/123.13; 536/127; 127/30; 127/42; 127/46.1; 127/47; 127/58
[58] Field of Search .......................... 536/4.1, 115, 119, 536/123.13, 127; 127/30, 42, 46.1, 47, 58

[56] References Cited

U.S. PATENT DOCUMENTS 5,298,611   3/1994   Navia et al. .......................... 536/4.1

OTHER PUBLICATIONS duPont Technical Information Bulletin "DMF—Recovery and Purification", Aug, 1987.
Johnson et al., "Salt Effect in Vapor–Liquid Equilibrium—Part II", Can. J. Chem. Eng. 38, 78–87 (1960).

*Primary Examiner*—Nathan M. Nutter
*Attorney, Agent, or Firm*—Charles J. Metz

[57]   ABSTRACT

There is disclosed a process for recovering sucralose-6-ester from a feed mixture of 6-O-acyl-4,1',6'-trichloro-4,1',6'-trideoxygalactosucrose in a reaction medium comprising a tertiary amide (such as N,N-dimethylformamide), wherein said process comprises removing a major proportion of said tertiary amide by steam distillation. In preferred aspects of the invention, the steam distillation is followed by extraction and then purification by crystallization or crystal aging to recover sucralose-6-ester in good yield.

9 Claims, 2 Drawing Sheets

RECOVERY OF SUCRALOSE INTERMEDIATES

CROSS-REFERENCE TO RELATED APPLICATIONS

This application is a continuation of application Ser. No. 08/198,744, filed on Feb. 18, 1994, and now abandoned which in turn was a continuation-in-part of copending application Ser. No. 08/030,518, filed Mar. 12, 1993, now U.S. Pat. No. 5,298,611.

The invention relates to a process for the recovery of sucralose intermediates.

BACKGROUND OF THE INVENTION

The artificial sweetener 4,1', 6'-trichloro-4,1', 6'-trideoxygalactosucrose ("sucralose") is derived from sucrose by replacing the hydroxyls in the 4, 1', and 6' positions with chlorine. In the process of making the compound, the stereo configuration at the 4 position is reversed. Therefore, sucralose is a galactosucrose having the following molecular structure:

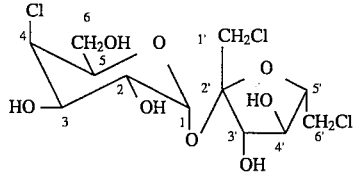

The direction of the chlorine atoms to only the desired positions is a major synthesis problem because the hydroxyls that are replaced are of differing reactivity; two are primary and one is secondary. The synthesis is further complicated by the fact that the primary hydroxyl in the 6 position is unsubstituted in the final product.

A number of different synthetic routes for the preparation of sucralose have been developed in which the reactive hydroxyl in the 6 position is first blocked, as by an ester group, prior to the chlorination of the hydroxyls in the 4, 1' and 6' positions, followed by hydrolysis to remove the ester substituent to produce sucralose. Several of such synthesis routes involve tin-mediated syntheses of sucrose-6-esters. Illustrative are the tin-mediated routes disclosed by Navia (U.S. Pat. No. 4,950,746), Neiditch et al. (U.S. Pat. No. 5,023,329), Walkup et al. (U.S. Pat. No. 5,089,608—"Walkup et al.-I"), and Sankey et al., U. S. patent application Ser. No. 08/030,930, filed Mar. 12, 1993.

The sucrose-6-esters produced by the above-cited synthesis routes are typically chlorinated by the process of Walkup et al., U.S. Pat. No. 4,980,463 ("Walkup et al.-II"). The chlorination process produces as a product a sucralose-6-ester, such as 4,1',6'-trichloro-4,1',6'-trideoxygalactosucrose-6-acetate ("TGS- 6-Ac"—when the sucralose-6-ester is the acetate ester) in solution in a tertiary amide, typically N,N-dimethylformamide ("DMF"). In one aspect, this invention provides a process for the recovery of the TGS-6-ester from the solution in tertiary amide that is the product of the chlorination process of Walkup et al.-II.

BRIEF SUMMARY OF THE INVENTION

The invention provides a process for recovering sucralose-6-ester from a feed mixture of (a) 6-O-acyl-4,1', 6'-trichloro-4,1', 6'-trideoxygalactosucrose, (b) salt including alkali metal or alkaline earth metal chloride, (c) water, and (d) other chlorinated sucrose by-products, in a reaction medium comprising a tertiary amide, wherein said process comprises removing said tertiary amide by steam distillation, to produce an aqueous solution of (a), (b) and (d) from which a major proportion of the tertiary amide in said feed mixture has been removed.

DETAILED DESCRIPTION OF THE INVENTION

Figure 1:
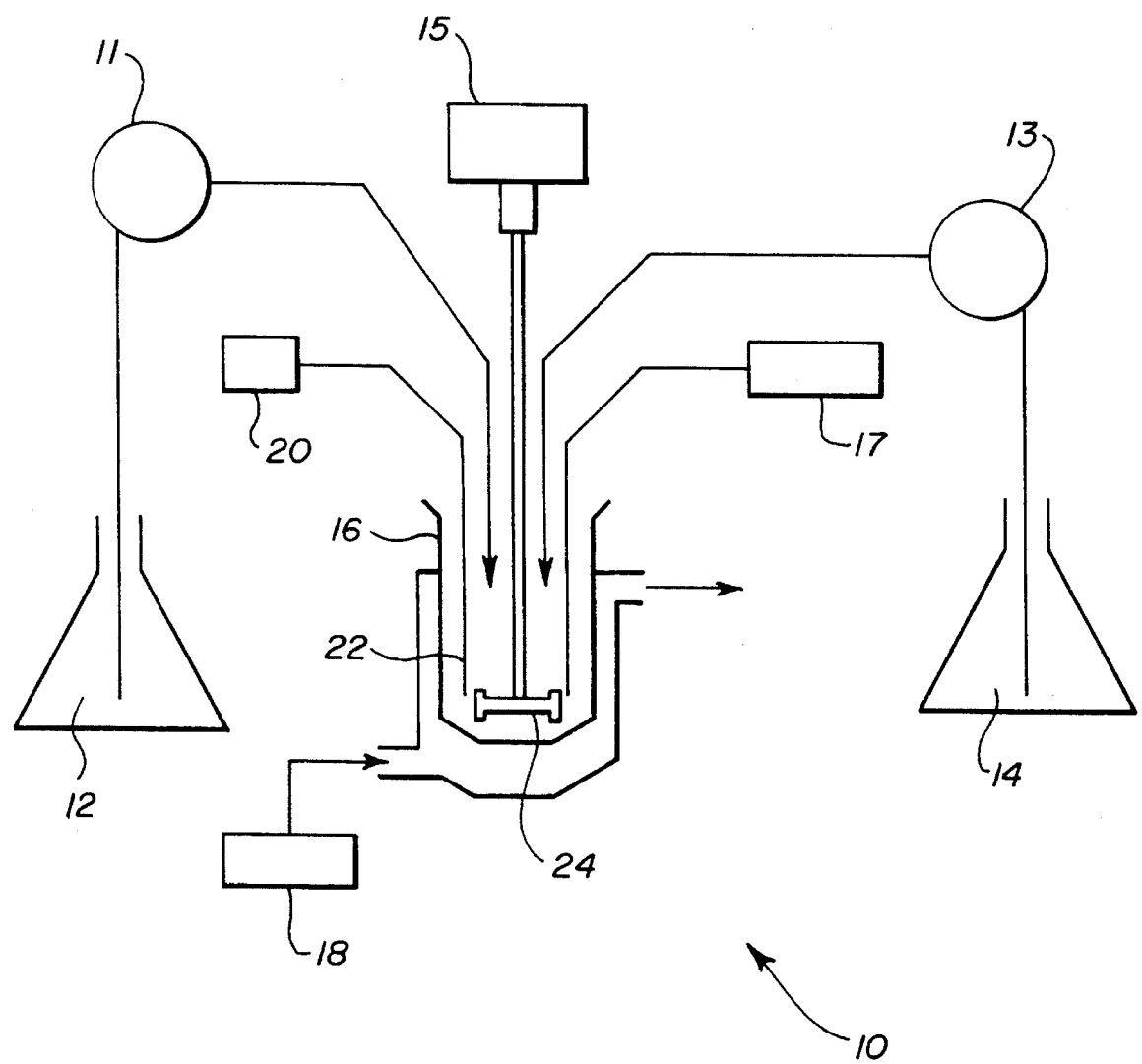
FIG. 1 is a diagram of a laboratory-scale dual-stream quench apparatus.

The process of the invention employs as its feed mixture a composition comprising 6-O-acyl-4,1', 6'-trichloro-4,1',6'-trideoxygalactosucrose in a tertiary amide (preferably DMF) reaction medium, such as the neutralized (quenched) product of the chlorination reaction described by Walkup et al.-II, cited above. The preferred 6-O-acyl-4,1',6'-trichloro-4,1',6'-trideoxygalactosucrose esters are 6-O-acetyl-4,1', 6'-trichloro- 4,1',6'-trideoxygalactosucrose and 6-O-benzoyl-4,1',6'-trichloro-4,1', 6'-trideoxygalactosucrose On the laboratory scale, the crude chlorination product may be quenched in a batch operation by the addition (in one portion) of one molar equivalent (basis phosgene) of ice-cold aqueous solutions or slurries of the alkali or alkaline earth metal hydroxides following the teachings of Walkup et al.-II. Preferred alkaline agents include the hydroxides of sodium, potassium, and calcium. More dilute aqueous alkaline solutions, such as for example 3 to 4N sodium hydroxide, are preferred. Broader ranges of concentration can be used (such as, for example, 2 to 8N sodium hydroxide). At the lower concentrations, precipitation of salts is reduced or avoided, which significantly reduces the amount of solids the process stream must accommodate. However, when the concentration becomes too low (e.g., below about 2N), the product stream becomes diluted to an extent that adversely affects the efficiency of the process.

In a preferred method of practice of this quench method, cold aqueous alkali is added with vigorous stirring as rapidly as possible in a quantity sufficient to raise the pH to 8–10. After stirring several minutes at this mildly elevated pH, the quenched solution is neutralized to pH 5–7 by the addition of an acid, such as, for example, concentrated aqueous hydrochloric acid or glacial acetic acid. The brief treatment of the quenched chlorination reaction mixture at pH 8–10 has the beneficial effect of insuring that all of the hydroxyl groups that have not been replaced by chlorine atoms are returned to their original hydroxyl group form (i.e., they are deprotected).

The batch method for quenching the crude chlorination product mixture suffers from scale limitations owing to inefficiencies in heat and mass transport. An improved method, known as the "dual-stream" or "concurrent addition" method, involves mixing streams of aqueous alkali and cooled (to about room temperature) crude chlorination product together at carefully metered rates with vigorous agitation under conditions of pH and temperature control. The primary advantages of the dual-stream quench method are that it provides for complete control of pH, temperature, and rate of mixing throughout the course of the quench. Thus, side reactions resulting in product losses are minimized. A further advantage of the dual-stream quench method is that it may be operated continuously by using a quench vessel fitted with either a bottom drain or a pump. By operating the dual-stream quench method in a continuous mode, a relatively large amount of crude chlorination product can be processed using a quench vessel of modest size. This continuous operation is a rough approximation of an in-line mixing process that might be employed for quenching in a commercial operation.

A diagram of a laboratory-scale dual-stream quench apparatus 10 is shown in FIG. 1. The laboratory-scale dual-stream quench apparatus 10 consists of a temperature-compensated pH control pump 11 for the addition of aqueous alkali 12, a second pump 13 for the constant addition of the crude chlorination product mixture 14, a quench vessel 16 fitted with an external jacket to allow for the flow of coolant, a thermostated chiller 18 to both cool and pump the coolant, and various pieces of auxiliary equipment such as a mechanical stirrer 15, thermocouples 17, etc. The apparatus is operated by adding the crude chlorination product mixture to the vessel at a constant rate. The pH control pump 11 is fitted with a pH meter 20 and a pH probe 22 which is placed in the quench vessel. The control pump 11 adds aqueous caustic automatically in response to programmed instructions for maintaining the pH of the mixture at a certain value. Vigorous agitation of the solution in the quench vessel is required. Experiments have indicated that inadequate mixing will result in domains of inadequate pH control within the quench mixture, resulting in the loss of product to side reactions.

Using a 1500-ml jacketed quench vessel, it was determined that crude sucralose-6-ester product mixtures could be quenched efficiently using a chlorination mixture constant feed rate of about 10 ml per minute, a quench mixture temperature of about 15° C. (coolant temperature 5° C.), a four-bladed propeller-type stirrer 24 with a stirring rate sufficient to insure good mixing, and a pH control setting of pH 8.5 on the pH control pump. These results were obtained with 3N or 4N NaOH as the alkaline agent, and with a starting charge of about 100 ml of between 3:1 to 1:3 DMF-$H_2O$ in the quench vessel (in order to have sufficient solution volume for accurate pH measurement during the early stages of the quench).

DMF REMOVAL

Following the quench, sucralose-6-ester is recovered from a feed mixture containing DMF (or other tertiary amide), water, salts, and chlorinated carbohydrate byproducts. When sodium hydroxide is used in the quench step and the tertiary amide is DMF, the salts that are formed include sodium chloride, dimethylamine hydrochloride and small amounts of sodium formate. The direct extraction of sucralose-6-ester from the quenched product mixture is complicated by the presence of DMF (or other tertiary amide) and its propensity to distribute between both organic and aqueous phases in the extraction step, which is the next step in the process sequence for producing sucralose. By so doing, the tertiary amide dissolves sucralose-6-ester in both phases, and also tends to dissolve other materials present in both phases, which makes recovery of the sucralose-6-ester in good yield difficult and/or expensive. Also, the presence of DMF or other tertiary amide interferes with the efficiency of the recovery of sucralose-6-ester by crystallization from the extraction solvent. This problem is particularly apparent in the recovery of a second crop of product from the first crystallization step, which is necessary in order to achieve good yields of the product.

The steam stripping operation is carried out so as to remove a major proportion of the DMF (or other tertiary amide) in the quenched feed mixture. It is desired to remove at least 95%, and preferably, from about 98 to 99.9% of the DMF present in the feed mixture, in order to avoid the undesirable consequences outlined in the previous paragraph.

In accordance with the present invention, it has been determined that DMF can be removed from the quenched chlorination product mixture by steam distillation without any detectable decomposition of the desired chlorination product. Attempts to remove DMF by fractional distillation was not successful, because fractional distillation proved to be quite inefficient from an energy standpoint. Also, and more importantly, fractional or simple distillation techniques fail because quenched feed contains salts at near their saturation level; thus, removal of any significant amount of water or DMF causes the salts to precipitate, in turn necessitating the addition of more water. DMF can also be removed by azeotropic distillation by adding a third solvent (e.g., p-xylene) that will form an azeotrope with DMF. The use of azeotropic distillation is not desirable because of the requirement for an additional solvent and the added equipment needed to handle the additional solvent.

Upon removal of the DMF (or other tertiary amide) by steam stripping, the DMF is effectively replaced with water in the process stream and the DMF can subsequently be recovered from the aqueous overheads by distillation and can be recycled.

Figure 2:
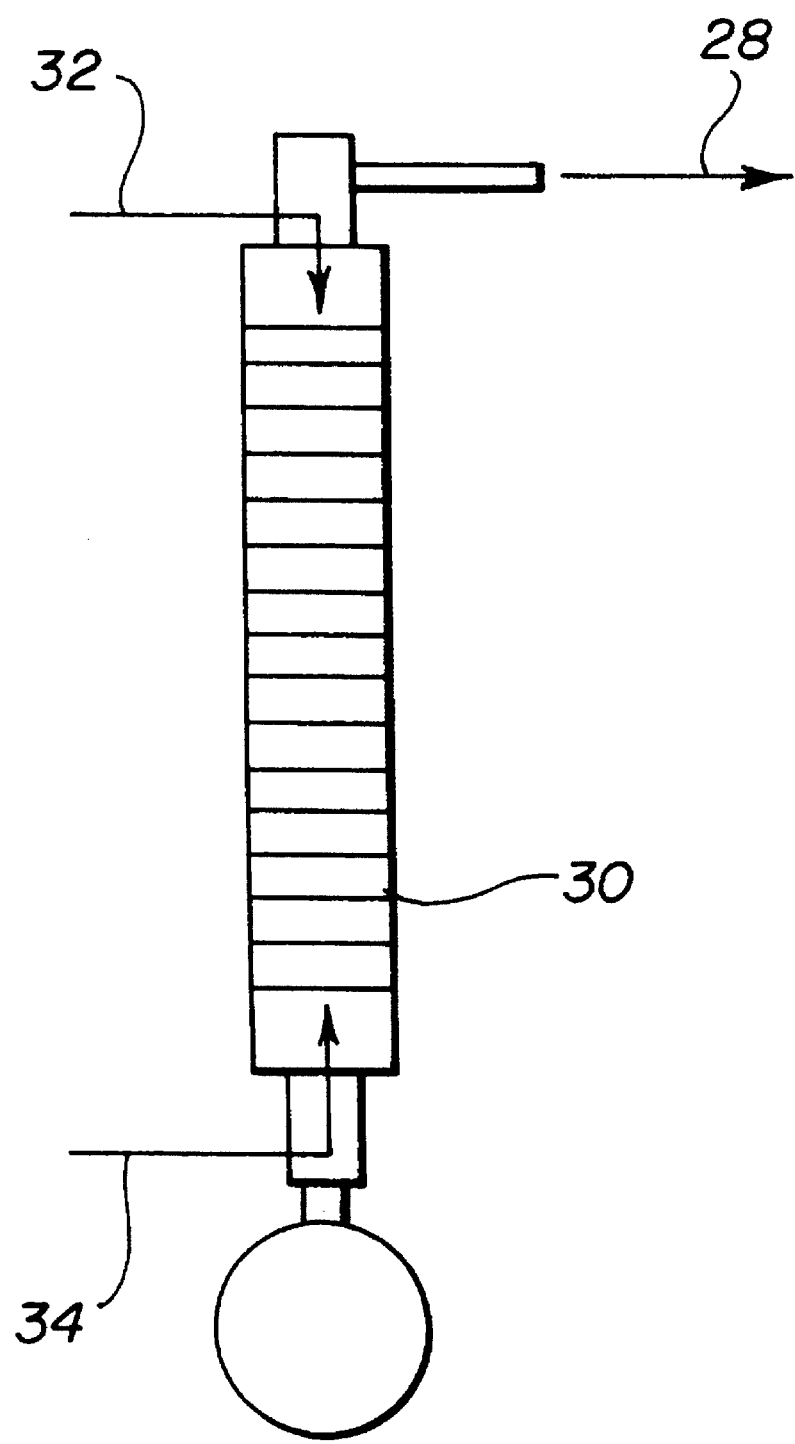
FIG. 2 is a diagram of a laboratory-scale falling-film packed-column steam distillation apparatus designed for stripping tertiary amide solvent from quenched sucralose-6-ester chlorination product.

An example of a laboratory-scale falling-film packed-column steam distillation apparatus designed for stripping the DMF from quenched sucralose-6-ester chlorination products is shown in FIG. 2. The stripping column is a 5.0 cm diameter, 90 cm long vacuum-jacketed distillation column packed with 5 mm Raschig rings or other suitable packing. Alternatively, a 15-plate, jacketed, Oldershaw column 30 has been used. The quenched product 32, which is typically preheated, is introduced into the top of the column at a rate of about 5.0–5.5 grams per minute. Steam 34 is introduced into the column through a sidearm located at the bottom of the column. As condensate-free steam is required, the steam is passed through a "preboiler" to trap any condensate carried over. In the laboratory, this preboiler is typically a small multineck flask fitted with a heating mantle. Typical steam feed rates are in the range of 38–47 grams per minute (calculated by adding the weights of overhead 28 and bottom products, and then subtracting the weight of chlorination feed), which corresponds to a steam-to-feed ratio ranging from 4:1 to 12:1, with steam to feed ratios of between 7.5:1 and 9:1 being typical for the packed column assembly. The preferred embodiment would use more plates with a lower steam:feed ratio, e.g., 15 plates with a steam/feed ratio of about 4:1.

The preheating of the quenched chlorination feed before it is introduced onto the top of the column is conducted in order to increase the efficiency of the stripping operation. Preheating is typically conducted in the laboratory by passing the feed through an enclosed glass coil apparatus heated with a secondary source of steam. The feed is normally heated to about 90°–95° C. The efficiency of DMF removal can also be enhanced by employing a "reboiler" (i.e., by heating the bottoms product in such a way that it refluxes up into the stripping column).

Temperatures are advantageously measured at two places on the apparatus using thermocouple devices. In addition to the quenched chlorination feed temperature described above, the temperature of the vapors passing through the distillation column head are also measured. Head vapor temperatures are typically in the range of from about 99° C. to about 104° C.

A typical quenched chlorination product of sucrose-6-acetate contains about 1.5–5 wt % sucralose-6-ester, about 0.5–1.5 wt % of various other chlorodeoxysucrose derivatives, about 35–45 wt % DMF, about 35–45 wt % water, and about 12–18 wt % salts. After passage of such product mixtures through the laboratory-scale steam-stripping apparatus, bottoms products will typically consist of about 1–3 wt % sucralose-6-ester, about 0.3–1.0 wt % of various other chlorodeoxysucrose derivatives, about 0.1–0.5 wt % DMF, about 80–90 wt % water, and about 8–12 wt % salts (expressed as NaCl, based on sodium and chloride assays).

Under typical laboratory conditions, which involve a column residence time of 7–10 minutes, no decomposition of sucralose-6acetate is detectable, provided the pH of the quenched chlorination feed is neutral to slightly acidic (pH 5.0–7.0).

SUCRALOSE-6-ESTER EXTRACTION

Following the steam strip, sucralose-6-ester may be readily isolated by extraction of the DMF-depleted aqueous brine solution with a variety of organic solvents. These solvents include methyl acetate, ethyl acetate, methyl ethyl ketone, methyl isobutyl ketone, methyl iso-amyl ketone, methylene chloride, chloroform, diethyl ether, methyl tert-butyl ether, and the like. A preferred solvent, for reasons of extraction selectivity, ease of recycle, and toxicological safety, is ethyl acetate.

Sucralose-6-ester isolation is typically conducted in the laboratory by first partially evaporating the crude steam-stripped product. About half the water present may optionally be removed, producing a solution containing about 2–5 wt % carbohydrates and about 15–25 wt % salts. Isolation is normally conducted by carrying out three sequential extractions with ethyl acetate or other appropriate solvent. The extracts are combined, and may optionally be washed with water (to partially remove any residual DMF and dichlorodideoxysucrose derivatives which to some extent are partitioned into the organic phase).

Once the crude sucralose-6-ester has been recovered from the aqueous brine as a solution in an appropriate organic solvent, it is concentrated and the product can be purified by crystallization and recrystallization from the same solvent until the required purity is achieved. An alternative to recrystallization is the process of crystal aging in the same solvent. In this process, the solid is agitated in fresh solvent for a time and at a temperature sufficient to allow an equilibration to occur between the concentration of impurities in the crystal and in the solvent. The process also allows a normalization of particle size distribution by dissolving fines and allowing other small particles to grow, while larger crystals are broken down. Either process can achieve the required purification of the TGS-6-ester.

Another noteworthy aspect of the purification/recovery process described above (that is, extraction followed by crystallization or aging) is that the same solvent can be used for extraction and the purification step. Typically (i.e., with other chemical materials), it is rare that the chemical product to be purified will crystallize from the same solvent that is used to extract it. In the present case, however, a combination of dilution and low levels of impurities allows the sucralose-6ester to remain in solution during the extraction, and then after the solution containing the extracted sucralose-6-ester is concentrated, the sucralose-6-ester product can then be crystallized from the same solvent.

It is noteworthy that TGS-6-Ac has relatively high solubility in anhydrous ethyl acetate, but its solubility is significantly reduced when ethyl acetate contains small amounts of water, e.g. from 2% to 4% by weight based on weight of ethyl acetate Thus, the use in the crystallization procedures of ethyl acetate containing sufficient water to significantly reduce the solubility of TGS-6-Ac, permits recovery of the desired product in sufficient yield to make the process economical.

EXPERIMENTAL

Chlorination of Sucrose-6-Acetate

A solution of crude sucrose-6-acetate in DMF (1.447 Kg) containing 416.94 g (1.084 moles) sucrose-6-acetate was diluted with 2.51 kg fresh DMF. The solution was cooled to −2° C. (dry ice/acetone/water bath) and stirred vigorously while phosgene (1.125 Kg, 99%, 11.26 moles) was added at a rate of 5.4 to 6.7 g/min. The temperature of the mixture was kept at 5°–12° C. during most of the addition.

The reaction mixture was allowed to stir at ambient temperature for 30 minutes, then heated to 115° C. over a 2–3 hour period, then held at 115°±1° for 1.75 hrs, then cooled to 35° C. over 30 min. The final mass, 4.34 kg, was carried on to the dual stream caustic quench and further processing.

DUAL STREAM QUENCH

The chlorinated mixture (typically about 3.5–4.5 kg) was pumped with an FMI Lab pump (model RP-G20) at 10 ml/min into a jacketed, 2-L resin kettle (without the top) with stopcock at the bottom, containing 200 ml of 1:1 mixture of DMF-water. Aqueous NaOH (3N, 12%) 5 kg, was delivered at the same time by a pH-controlled prominent pump with the pH set point at 9.0 and pump stroke set to 25%. The proportional bandwidth was at the maximum setting (± 1 pH unit) to minimize any overshoot of pH. The jacket temperature of the quench flask was controlled with Forma Scientific circulating bath. The jacket temperature was maintained at 5° C. The temperature of the quench mixture was initially at 6° C., and rose to 20° C. in the first 10 minutes. Thereafter, the temperature stabilized at about 17° C. over the entire period of quench. During the quench, pH fluctuated between 8.0 to 8.5 in the flask. The mixture was vigorously agitated with a heavy-duty laboratory stirrer. The quenched mixture was removed from the vessel in portions as the quench vessel filled to capacity. Each batch was quenched in approximately 6 hours at the above conditions. For most batches, approximately 9 kg of quenched mixture were obtained. 4,1',6'-Trichloro- 4,1',6'-trideoxygalactosucrose-6-acetate ("TGS-6-Ac") was present at 2%-wt in the mixture. The conditions and parameters were optimized to achieve less than 2 mole-percent deacetylation during quenching.

All the quenched batches were vacuum filtered to remove insoluble particulate matter using either vacuum filtration through a sintered glass Buchner funnel or centrifugation. The filtrate was sampled for analysis and carried on to steam stripping.

STEAM STRIPPING

1. Laboratory Scale:

The quenched mixtures were steam stripped in batches. Two things were accomplished via steam stripping—1) removal of DMF to ease extraction, 2) removal of tarry, polymeric soluble material found in quenched mixtures. The steam stripping was carried out in a well insulated 4 foot tall glass column with an I.D. of 4 inches. The conditions were optimized to obtain less than 1% DMF in the bottoms. The column was packed with ¼" size Raschig rings. The steam to feed ratio was maintained in the range of 6 to 8. After every three batches steam stripped, the column was cleaned with 1N caustic solution, which removes the tarry, polymeric materials from the packing and column surfaces. A typical run of steam stripping was completed in 6 hours time. For every 9 kg batch of feed, approximately 13 kg of steam-stripped bottoms were produced with a TGS-6-Ac concentration of about 1.5%-wt.

The usual method of operation was to pump the quenched, filtered mixture with an FMI Lab pump (RP-G20) through a preheater, consisting of a 4" Graham-type condenser with steam in the jacket, then directly into the center of the top of the column. Steam was passed through a reboiler (a 3-neck, 500 ml flask with a magnehelic low pressure gauge, and a heating mantel) to remove condensate before entering the column at the bottom below the packing. Column pressure remained at 0–3 in. of water throughout the operation. Feed rate was determined initially by timing the pumping rate from a graduated reservoir. The bottoms collection rate was measured by collecting in a graduated receiver. The distillation rate was measured, by condensing the effluent from the top of the column, as ml/min. The steam rate was determined by difference (STEAM=TOPS+BOTTOMS–FEED).

2. Larger Scale Steam Stripping:

Chlorinated and quenched process streams, of composition similar to preceding laboratory scale examples, were fed above the top tray of a 10 inch diameter column containing 20 sieve trays while steam was directed into the bottom of the column. A steam/feed ratio of approximately 3 was maintained to achieve the desired removal of DMF in the bottoms stream (> 99.2% removal based on assayed amount of DMF charged to the column in the feed). Pre-heating the feed stream to 80°–90° C. was beneficial in improving the stripping efficiency in the column. The DMF/Water stream is stripped overhead by the counter-current steam flow. The column bottoms containing the TGS-6-Ac, salts and water was delivered to the next process area for purification. The overheads are sent to another column for DMF recovery ( typical composition 12% DMF, 88% water). In this manner, quenched feed containing 1.8% TGS-6-Ac, 8.5% salts, 54.6% water, and 30.4% DMF, was stripped to produce bottoms containing 1.6% TGS-6-Ac, 9.8% salts, 84.9% water, and 0.1% DMF residual (99.6% removal of DMF). The ratio of steam strip feed mass to bottoms mass was about 1.22.

EXTRACTION

1. Batch Extraction:

Each laboratory scale batch of steam stripped bottoms material (approximately 13 kg) was extracted with a total of 12 gallons of ethyl acetate in three portions (first extraction with 6 gallons, second and third extractions with 3 gallons each). The extracts obtained from each batch were distilled on rotary evaporator for ethyl acetate recovery and recycling. The raffinates from each batch were properly disposed off for waste treatment. For each batch, steam stripped bottoms, ethyl acetate extracts, raffinates and recovered ethyl acetate were analyzed. The concentrated extracts from each batch (typically 1.25 kg; TGS-6-Ac concentration about 25%-wt) were then carried on to crystallization.

2. Counter-Current Extraction of Steam Strip Bottoms:

Counter-current extractions were done using a Robatel Model UX 1.1 four-stage mixer-settler battery. Feed and solvent were pumped at known rates using Masterflex Model 7518-10 peristaltic pumps calibrated with the respective solvents. Water saturated ethyl acetate was used as the extractant. Steam strip bottoms, of a composition as described in previous examples, was extracted using a 1:1 solvent to feed ratio (99% extraction of TGS-6-Ac into ethyl acetate).

CRYSTALLIZATION OF TGS-6-Ac With Recycle of Mother Liquor

FIRST CRYSTALLIZATION (K1): The concentrated ethyl acetate extract (1.571 kg—from the laboratory scale extractions) was concentrated to half-volume to azeotropically remove as much water as possible. The residue was combined with the mother liquor (833.1 g) from second crystallization (K2) of the previous batch, the second crop solid (K4) (22 g) also from the previous batch and 20 g of water. The mixture (estimate 1.1 kg; 17.4% TGS-6-Ac; 62.9% of total carbohydrates) was transferred to a jacketed 2-L, 4-neck, round-bottom flask equipped with overhead stirrer, thermocouple thermometer, condenser and stopper. The jacket temperature was controlled with a circulating bath (Forma Scientific, model 2006). The mixture was warmed to 62° C. (69° C. jacket) to re-dissolve the solid and an analytical sample (16.6 g) withdrawn.

The mixture was cooled from 62.3 to 55.5° C. over 31 min., at which point the solution was seeded with a few milligrams of pure TGS-6-Ac; crystallization began 7 min. later. The temperature was raised 2° C. for 22 min. to slow the rate of crystallization; then cooled to 53° C. over 2.5 hr.; to 42.6° C. over 2.3 hr.; and to 24.9° C. over 1.75 hr.

The crystalline product was recovered by filtration of the mixture under vacuum through a sintered glass funnel with a paper disk, into a tared filtration flask. The filter cake was pressed firmly to dewater it, then it was washed with about one volume (122.2 g) of water-soaked ethyl acetate. The filter cake was air dried (220.5 g, wet; 73.1% TGS-6-Ac; 94.8% of total carbohydrates).

SECOND-CROP CRYSTALLIZATION OF TGS-6-Ac (K4): The mother-liquor from the first crystallization (990.7 g) was concentrated to 230 g; diluted with 180 g fresh ethyl acetate and 8 g water; warmed in a 65° C. water bath and allowed to cool and crystallize over night. The solid product was recovered as described above; 25.3 g (wet; 63.06% TGS-6-Ac; 82.9% of total carbohydrates). Filtrate was discarded.

SECOND CRYSTALLIZATION (K2): Once-crystallized TGS-6-Ac (215 g) was combined with the mother-liquor from the third crystallization of a previous batch (387.5 g; 1.66% TGS-6-Ac), 20 g water and 409 g ethyl acetate. The mixture (1.03 kg; 16.55% TGS-6-Ac) was dissolved by heating in the crystallization flask to 62.5° C.; cooled to 59° C.; seeded as for K1; cooled to 56.8° C. over 0.75 hr (solution became turbid with crystals); cooled to 44.7° C. over 5.5 hr; cooled to 20.1° C. over 1.5 hr. Solid TGS-6-Ac (181.9 g; 74.61%) was recovered as before, air-dried and carried to the final crystallization (K3).

THIRD CRYSTALLIZATION (K3): Twice crystallized TGS-6-Ac (179 g) was dissolved in 700 g ethyl acetate and 18 g water at 64° C.; the solution was cooled to 60.4° C. over 24 min., and seeded; at 59° C. (38 min.) crystallization began; cooled to 55.1° C. over 2.3 hr.; cooled to 44.7° C. over 5 hr.; cooled to 20.3° C. over 2.3 hr. TGS-6-Ac was recovered and washed as before, dried at 40° C. in vacuo overnight to give 130.2 g of dry solid (80.52% TGS-6-Ac; 99.3% of total carbohydrates) which was carried to deacetylation.

Alternative Purification Procedure—Crystal Aging:

A 1 kg sample of the dilute extracts from the countercurrent extraction procedure was concentrated such that the composition corresponded to about 8.7% wt/wt TGS-6-Ac (144.7 g). The water content, as evaluated by Karl-Fischer assay, was adjusted to about 4% wt/wt. The mixture was cooled at 1° C./5 min until the first crystals appeared. Then the mixture was warmed at the same ramp rate until all solids re-dissolved (pot temperature= 49° C.). This was cooled to 40° C., and 0.5 g of 99.9% pure TGS-6-Ac, having a particle size distribution centered @60 micron was added. The mixture was stirred gently at 150 rpm (minimum rate to prevent settling) and the temperature was reduced to 20° C. over an 8 hour period followed by stirring at ambient temperature overnight. The crystals were isolated by centrifugation at about 1000 rpm using an IEC model 450 bench top centrifuge and a Kevon #184-DA multifilament polyester centrifuge bag rated for 35 cfm. The slurry was transferred at 75 mL/min using a Masterflex peristaltic pump. When feeding was complete and the flow of liquor subsided, the speed was increased to about 1500 rpm until no more liquor was discharged. The crystals were washed with ice-cold water-saturated ethyl acetate (2×200 mL). The crystals were manually distributed before adding wash solvent to ensure thorough washing. The wash solvent was added while centrifuging at 1000 rpm, then the rate was increased to 1500 rpm after complete addition until no further liquor discharged. Damp solid (147.6 g) was obtained which was 71.7% TGS-6-Ac by HPLC assay, representing 73.1% recovery. Purity was 96.93 wt % by HPLC; 95.89% by GLC. The particle size distribution was symmetrical and centered around 50 microns.

FIRST AGING (A1)

The sample remaining after assay of the foregoing (142.56 g) was slurried in a mixture of ethyl acetate (957.8 g) and water (39.9 g), resulting in a slurry approximately 8.9% TGS-6-Ac and 4% water by weight, and containing 102.18 g TGS-6-Ac. The mixture was stirred gently, and the bath programmed to heat to 40° C., then cool to 20° C. over 8 hours, followed by a two hour hold. The slurry was centrifuged and the cake washed (2×120 mL) as before, yielding damp A1 solid (80.89 g) which was 79.38 wt % TGS-6-Ac by HPLC (corresponds to 62.84% recovery). The purity was 99.56 wt %, and the particle size was bimodal, mainly centered around 125 microns with a slight second peak at 300 microns.

SECOND AGING (A2)

The remaining damp A1 solid (175.89 g) was slurried in a mixture of ethyl acetate (546.2 g) and water (22.8 g) resulting in a slurry containing approximately 9.38% TGS-6-Ac and 4.27% water by weight, and containing 60.24 g of TGS-6-Ac. The mixture was stirred gently, and cooled to 20° C. as before. The slurry was centrifuged and the cake washed (2×80 mL) as before, yielding damp A2 solid (52.8 g) 72.59 wt % TGS-6-Ac by HPLC, representing a 63.62% recovery. The purity was 99.44% by HPLC. The particle size distribution was symmetrical and centered around 175 microns.

The number of crystallization steps can be shortened by using a more dilute solution for the first crystallization step (K1), the second crystallization step (K2), or the first aging step (A1). Thus, where fewer processing steps are required, more dilute solutions can be employed than those set forth in the foregoing examples. Conversely, where equipment size is limiting and more concentrated solutions are to be used, then more steps are required. This operating principle is the gradual dilution of impurities in the crystals, either in fewer steps at greater dilution or in more steps at less dilution.

SUCRALOSE FROM PURIFIED SUCRALOSE-6-ACETATE

Purified sucralose-6-acetate which had been twice recrystallized from ethyl acetate (~145 g) was dissolved in methanol (2.175 L) and 25% sodium methoxide solution (7.2 ml). After 2 hours the de-acetylation reaction was complete (tlc chloroform/methanol/acetic acid 80:17:3) and the mixture clarified by filtration. The filtrate was passed down a column (50×2.5 cm) containing IRC50 ($H^+$) ion exchange resin (100 g) and was washed through with methanol (250 ml). The eluate was concentrated to a syrup to which water (500 ml) was added. The aqueous solution was concentrated and then made up to 1342 g with water. This aqueous solution was extracted with ethyl acetate saturated with water (670 ml) (cloudiness removed from aqueous phase) and the organic phase was backwashed with water saturated with ethyl acetate (670 ml). The combined aqueous phases (2090.73 g) and the organic layer (483.15 g) were sampled. The aqueous phase was concentrated to 175 g. The concentrate was determined to be 67.5% w/w sucralose by refractometry. The product was transferred to a crystallizer and washed in with water (40 ml). When water was added, an opalescent solution was obtained. Carbon (2 g) was added to the solution and after 5 mins. stirring the solids were filtered off and washed with water (50 ml). The clear filtrate was concentrated to 155.78 g (68.85% w/w sucralose by RI). The syrup was transferred to a crystallizer and washed in with water (40 ml). The solution was heated to 55° C. and seeded with damp sucralose (2.5 g). The cooling program was started after 1 hour at 55° C. The solution was cooled from 55° C. to 50° C. over 30 min, from 50° C. to 40° C. over 30 min and from 40° C. to 25° C. over 30 min. When the crystallization had been held at 25° C. for 2 hours the product was collected and dried in vacuo at 40° C. Yield: damp 82.93 g, dry 76.14 g (LOD 8.2%). Additional crystalline material began to separate slowly from the mother liquor (151.3 g) on standing.

What is claimed is:

1. A process for recovering sucralose-6-ester from a feed mixture of (a) 6-O-acyl-4,1',6'-trichloro-4,1',6'-trideoxygalactosucrose, (b) at least one salt selected from the group consisting of alkali metal chloride, alkaline earth metal chloride, dimethylamine hydrochloride, and alkali metal formate, (c) water, and (d) other chlorinated sucrose by-products, in a reaction medium comprising a tertiary amide, wherein said process comprises removing said tertiary amide by steam distillation, to produce an aqueous solution product of (a), (b) and (d) from which at least 95% of the tertiary amide in said feed mixture has been removed.

2. The process of claim 1 wherein from 98 to 99.9% of the tertiary amide in said feed mixture is removed by steam distillation.

3. The process of claim 1 wherein the 6-O-acyl- 4,1',6'-trichloro-4,1',6'-trideoxygalactosucrose is 6-O-acetyl- 4,1', 6'-trichloro-4,1',6'-trideoxygalactosucrose, and wherein the tertiary amide is N,N-dimethylformamide.

4. The process of claim 3 wherein the 6-O-acyl-4,1', 6'-trichloro-4,1', 6'-trideoxygalactosucrose is 6-O-acetyl-4,1',6'-trichloro-4,1',6'-trideoxygalactosucrose, and wherein the tertiary amide is N,N-dimethylformamide.

5. The process of claim 1 wherein the 6-O-acyl- 4,1',6'-trichloro-4,1',6'-trideoxygalactosucrose is 6-O-benzoyl-4,1',6'-trichloro-4,1',6'-trideoxygalactosucrose, and wherein the tertiary amide is N,N-dimethylformamide.

6. The process of any of claims 1, 2, 3, and 4 wherein said aqueous solution product is subjected to extraction by an organic solvent that dissolves the 6-O-acyl-4,1', 6'-trichloro-4,1', 6'-trideoxygalactosucrose.

7. The process of claim 6 wherein the organic solvent is ethyl acetate.

8. The process of claim 6 wherein the product of said extraction is subjected to purification by crystallization or crystal aging to recover the 6-O-acyl-4,1', 6'-trichloro-4,1', 6'-trideoxygalactosucrose.

9. The process of claim 8 wherein the purification is carried out in ethyl acetate containing from 2% to 4%, by weight, of water.

* * * * *